United States Patent [19]

Wissner

[11] 4,299,988
[45] Nov. 10, 1981

[54] 1-HYDROXYMETHYL-1-OXO-PROSTANE DERIVATIVES OF THE E SERIES

[75] Inventor: Allan Wissner, Ardsley, N.Y.

[73] Assignee: American Cyanamid Company, Stamford, Conn.

[21] Appl. No.: 203,753

[22] Filed: Nov. 3, 1980

Related U.S. Application Data

[63] Continuation-in-part of Ser. No. 961,032, Nov. 15, 1978, abandoned, which is a continuation-in-part of Ser. No. 858,589, Dec. 8, 1977, Pat. No. 4,206,822, Ser. No. 858,588, Dec. 8, 1977, Pat. No. 4,170,597, Ser. No. 858,580, Dec. 8, 1977, Pat. No. 4,197,245, Ser. No. 858,487, Dec. 8, 1977, abandoned, Ser. No. 858,504, Dec. 8, 1977, Pat. No. 4,172,837, and Ser. No. 858,579, Dec. 8, 1977, Pat. No. 4,212,969.

[51] Int. Cl.³ ............................................. C07C 49/395
[52] U.S. Cl. .................................................... 568/379
[58] Field of Search ......................................... 568/379

[56] References Cited

U.S. PATENT DOCUMENTS 3,751,463  8/1973  Caton et al. .................... 568/379
4,251,466  2/1981  Axen .............................. 568/379

OTHER PUBLICATIONS

Bergstom et al., J. Biol. Chem., vol. 238, 355 (1963).
Horton, Experientia, vol. 21, 113 (1965).

Primary Examiner—Natalie Trousof
Assistant Examiner—James H. Reamer

[57]  ABSTRACT

The invention disclosed herein relates to pharmacologically active prostaglandin derivatives of the E series having on the terminal methylene carbon of the alpha chain a hydroxymethylketo substituent

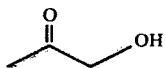

4 Claims, No Drawings

1-HYDROXYMETHYL-1-OXO-PROSTANE DERIVATIVES OF THE E SERIES

CROSS-REFERENCE TO RELATED APPLICATIONS

This application is a continuation-in-part of application Ser. No. 961,032 filed Nov. 15, 1978, now abandoned, which in turn a continuation-in-part of applications Ser. Nos. 858,589, U.S. Pat. No. 4,206,822, 858,588, U.S. Pat. No. 4,170,597; 858,580, U.S. Pat. No. 4,187,245; 858,487; 858,504 U.S. Pat. No. 4,172,837; and 858,579, now U.S. Pat. No. 4,212,969 each of which was filed on Dec. 8, 1977.

BRIEF DESCRIPTION OF THE INVENTION

This invention relates to the optically active compound of the formula

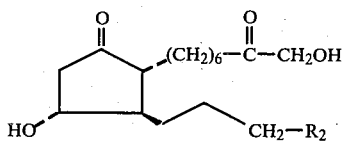

wherein $R_2$ is

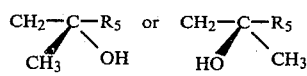

wherein $R_5$ is selected from the group consisting of $C_4$-$C_7$ alkyl and the racemic mixture thereof.

This invention also relates to the method of preparing the above-described compounds, as well as to novel intermediates useful for the preparation of the prostaglandin compounds described herein. The present invention will be fully described with reference to the flowsheets and examples of this application.

DETAILED DESCRIPTION OF THE INVENTION

The compounds of this invention are administered in various ways for various purposes, e.g., intravenously, intramuscularly, subcutaneously, orally, intravaginally, rectally, bucally, sublingually, topically and in the form of sterile implants for prolonged action.

For intravenous injection or infusion, sterile aqueous isotonic suspensions are preferred. For subcutaneous or intramuscular injection, sterile suspensions of the compounds in aqueous or non-aqueous media are used. Tablets, capsules, and liquid preparations such as syrups, elixirs, and simple solutions, with the usual pharmaceutical carriers are used for oral or sublingual administration. For rectal or vaginal administration, suppositories prepared as known in the art are used. For tissue implants, a sterile tablet or silicone rubber capsule or other object containing or impregnated with the substance is used. On certain occasions it may be advantageous to administer the compounds of this invention as clathrate compounds with substances such as α-cyclodextrin.

The prostaglandins are a family of closely related compounds which have been obtained from various animal tissues and which stimulate smooth muscle, lower arterial blood pressure, antagonize epinephrine-induced mobilization of free fatty acids, and have other pharmacological and autopharmacological effects in mammals. See Bergstom, et al., J. Biol. Chem., 238, 3555 (1963) and Horton, Experientia, 21, 113 (1965) and references cited therein. All of the so called natural prostaglandins are derivatives of prostanoic acid:

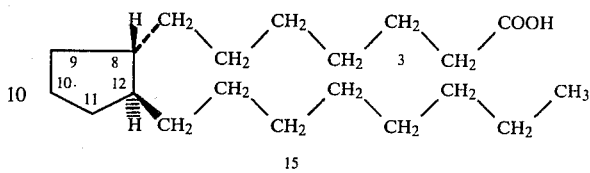

The hydrogen atoms attached to C-8 and C-12 are in trans-configuration. The natural prostaglandins represent only one of the possible optical isomers. The compounds of this invention include all possible optical isomers and racemates.

The configuration of substituents on the prostaglandin molecule are designed to be in the α-configuration if they lie beneath the plane of the molecule as drawn above and are designated with a ----bond. Those substituents which lie above the plane of the molecule as drawn above are designated β and are represented by a ⟍bond.

The compounds of this invention which have the structure as shown in formula (A) wherein Y is

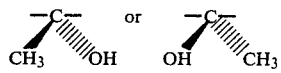

are said to be in the same configuration as the natural prostaglandins with respect to the configurations at $C_8$, $C_{11}$ and $C_{12}$ and are designated by the prefix nat. The enantiomer, represented by formula (B) is said to be in the mirror image or ent configuration. A substituent at $C_{11}$ drawn with a dotted line ($C_{11}$---OH) is said to have an α configuration; a solid line $C_{11}$—OH) indicates a β configuration. The configuration at Y will be expressed in terms of R and S as is understood in the art.

For example, the compound represented by formula (C) is named nat-(16S)-1,9-dioxo-11α,16-dihydroxy-16-methyl-1-hydroxymethyl-13-trans-prostene; its enantiomer (formula D) is named ent-(16R)-1,9-dioxo-11α,16-dihydroxy-16-methyl-1-hydroxymethyl-13-trans prostene. In a similar manner, the compounds represented by formulae (E) and (F) have the configurations shown below.

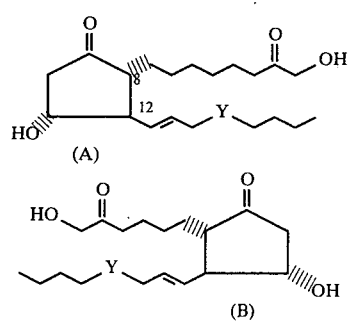

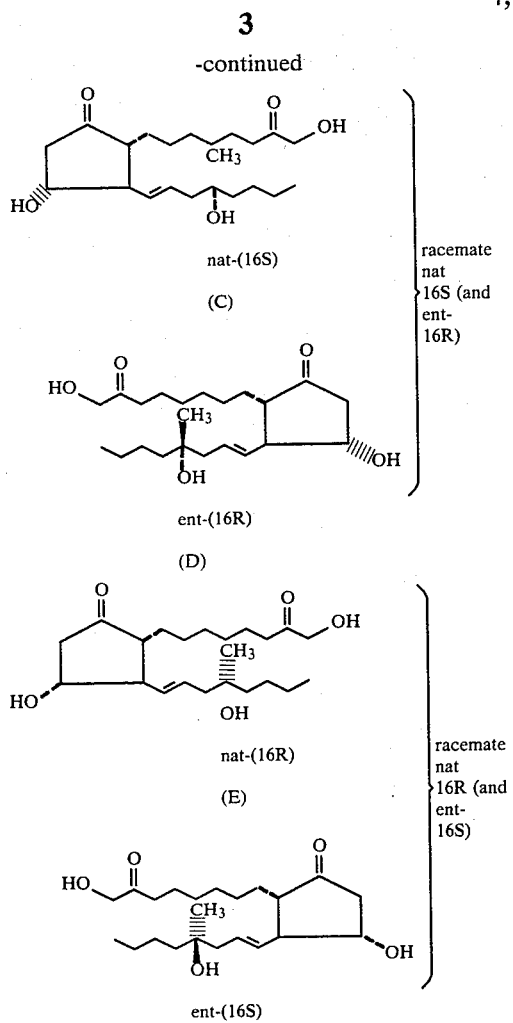

nat-(16S)

(C)

ent-(16R)

(D)

nat-(16R)

(E)

ent-(16S)

racemate nat 16S (and ent-16R)

racemate nat 16R (and ent-16S)

In each of the above formulae (C to F) the hydroxy group at $C_{11}$ is named "-11a-hydroxy".

The novel compounds of this invention can be prepared by a novel 1,4-conjugate-addition procedure involving treatment of the ether blocked cyclopentenone such as (129), (94) or (94A) with a lithio-cuprate reagent such as (117), (118), or (119) prepared as illustrated in the following Flowsheets.

The 1,4-conjugate-addition procedure is described hereinbelow in Flowsheet N. The preparation of the requisite 1-iodo-trans-1-alkenyl or 1-tributylstannyl-trans-;-alkenyl derivative is illustrated in the Flowsheets and the novel and important methods of preparation of the 4-hydroxycyclopentenones embracing the 1-(hydroxymethyl)-1-oxo a-chain is described in connection with Flowsheets I–M.

In accordance with the procedure as outlined in Flowsheet C, an aldehyde (34) is treated with propargylic magnesium halide to form the homopropargylic alcohol (35), which is converted to its trimethylsilyl ether in the usual manner. The silylated derivative is then treated with disiamylborane (prepared in situ in tetrahydrofuran solution at ice bath temperature from 2-methyl-2-butene, sodium borohydride and boron trifluoride ethereate) and then anhydrous trimethylamine oxide. The resulting solution and an iodine solution in tetrahydrofuran are added simultaneously to a sodium hydroxide solution to give the 1-iodo-4-trimethylsilyloxy-trans-1-alkene (36), precursors for various 16-hydroxyprostaglandins.

The trimethylsilyl protecting group is removed with mild acid and the resulting vinyl iodide alcohol is oxidized with pyridinium chlorochromate to provide the 1-iodo-4-oxo-trans-1-alkene (37), which upon treatment with a Grignard reagent ($R_{13}MgX$) provides the 1-iodo-4-hydroxytrans-1-alkene, which is silylated in the usual manner to provide the silyl ether (38) wherein $R_{11}'$ is lower alkyl ($C_3$ to $C_7$) and $R_{13}'$ is methyl.

FLOWSHEET C

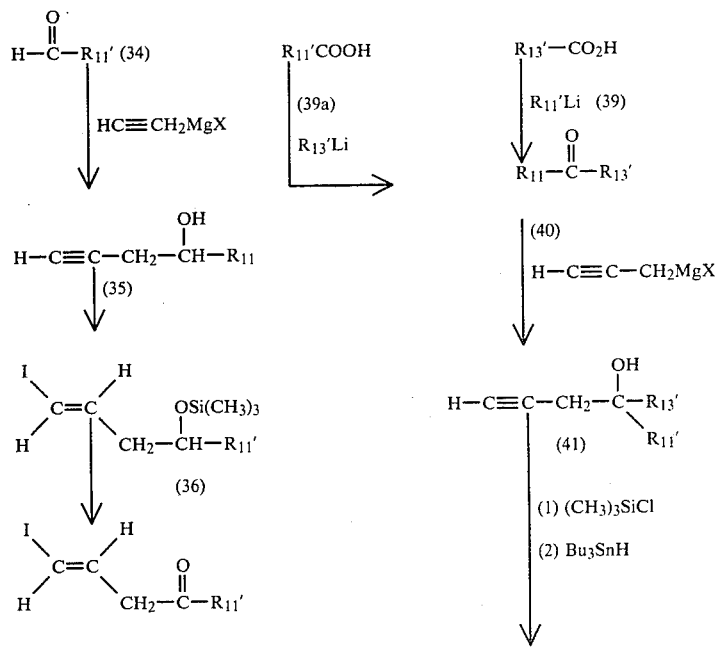

FLOWSHEET C

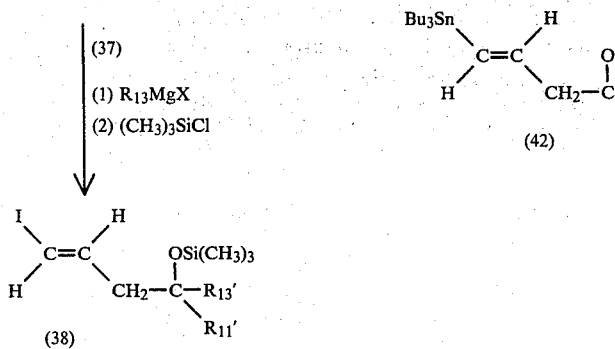

A more preferred method for the preparation of the vinyllithium precursor is also described in Flowsheet C. Treatment of the requisite carboxylic acid (39a or 39) with the appropriate organolithium reagent $R_{13}'Li$ or $R_{11}'Li$ respectively), wherein $R_{11}'$ and $R_{13}'$ are hereinabove defined, gives the corresponding ketone (40) which upon treatment with propargylic magnesium halide provides the homopropargylic alcohol (41) which is converted to the trans vinylstannyl derivative by sequential treatment with chlorotrimethylsilane and tri-n-butyltin hydride. Treatment of the vinylstannyl reagent (42) with n-butyllithium at a temperature of $-10°$ C. to $-78°$ C. generates the corresponding vinyllithium reagent.

FLOWSHEET D

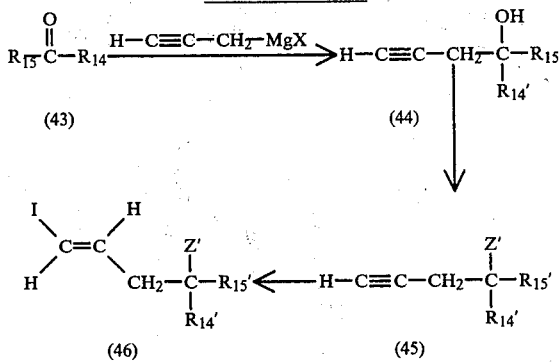

In accordance with Flowsheet D herein, the precursors for the other 16-hydroxy prostaglandins are prepared by treating an appropriate aldehyde or ketone (43) with a propargylic magnesium halide to yield the requisite homopropargylic alcohol (44). The alcohol is protected as a trimethylsilyl ether (45). These ethers are then converted to the appropriate trans-vinyliodide (46) by treatment with disiamylborane generated in situ from 2-methyl-2-butene, sodium borohydride, and boron trifluoride, followed by treatment with trimethylamine oxide and then iodine and sodium hydroxide, wherein $R_{15}$ and $R_{15}'$ are methyl $O-Si(CH_3)_3$; $R_{14}'$ is selected from the group comprising lower alkyl ($C_3$ to $C_5$).

The preparation of the cyclopentenones (68) of this invention containing the hydroxymethylketone feature wherein Z is $-(CH_2)_6-$ and $R_3$ a hydroxy group can be accomplished in several ways one of which involves the conversion of the corresponding cyclopentenone (69) containing a carboxylate function to the respective hydroxyketone analog (68).

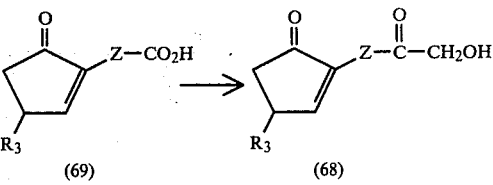

Most of the cyclopentenone carboxylic acids (69) required for the purposes of this invention have been described in the literature or can be prepared by procedures quite analogous to those already described. Appropriate references are provided in the examples which follow. The synthesis of certain non-reference requisite cyclopentenone carboxylic acids (69) is also described herein.

The conversion of the cyclopentenone carboxylic acid (69) to the respective hydroxyketone analogs (68) and the protection of these compounds for a conjugate addition reaction is described hereinbelow in Flowsheets K, wherein Z is $-(CH_2)_6-$.

The reaction of the hydroxy acid (87) with at least two equivalents of dimethyl-t-butyl-silylchloride in the presence of imidazole in dimethylformamide at 30°-40° C. gives the bis-dimethyl-t-butylsilated compound (88). The carboxylate dimethyl-t-butylsilyl group can be selectively removed by treatment with acetic acid, tetrahydrofuran and water (4:2:1) to give the carboxylic acid (89). The acid chloride (90) is prepared by first treating the acid (89) with sodium hydride in tetrahydrofuran to give the sodium salt. The resulting suspension of the sodium salt is then treated with oxalyl chloride in the presence of a catalytic amount of dimethylformamide. Alternatively the acid chloride (90) can be prepared directly by the reaction of the acid (89) or the dimethyl-t-butylsilyl ester (88) with oxalyl chloride in tetrahydrofuran in the presence of a catalytic amount of dimethylformamide at 0° C. The slow addition of an etheral solution of the acid chloride (90) to an etheral solution of two to three equivalents of diazomethane gives the diazoketone (91) which on acid hydrolysis gives the 4-hydroxy cyclopentenone (92) containing the hydroxyketone function.

Alternatively the acid chloride (90) can be heated with at least two equivalents of 1,1,2-tris-trimethylsilylethylene (80) at 90°-120° C. in the absence of a solvent to give compound (93) which is readily hydrolized and decarboxylated to give the 4-hydroxycyclopentenone (92) containing the hydroxyketone feature. Protection of 92 can be accomplished by treatment with an excess of a mixture of 2-methoxy-1-propene (84) and 2,2-dimethoxypropane (85) in benzene with an acid catalyst such as p-toluenesulfonic acid to give the bis-ketal (94) which is suitably protected for a conjugate addition reaction.

Alternatively, the two hydroxyl moieties may be protected using 2 equivalents of 2-methoxypropene per equivalent of 92 in the presence of a catalyst such as chloroacetic acid to provide compounds such as 94A.

Other useful protecting reagents are dihydro-2H-pyran, ethylvinylether and the like. Other acid sensitive protecting group for the two hydroxyl groups are the triloweralkylsilyls (from silylchlorides), triphenylmethane (from tritylchloride or bromide), mono-p-methoxytriphenylmethane (from mono-p-methoxytriphenylmethylchloride or bromide), methoxymethyl (from chloromethylmethylether) and the like.

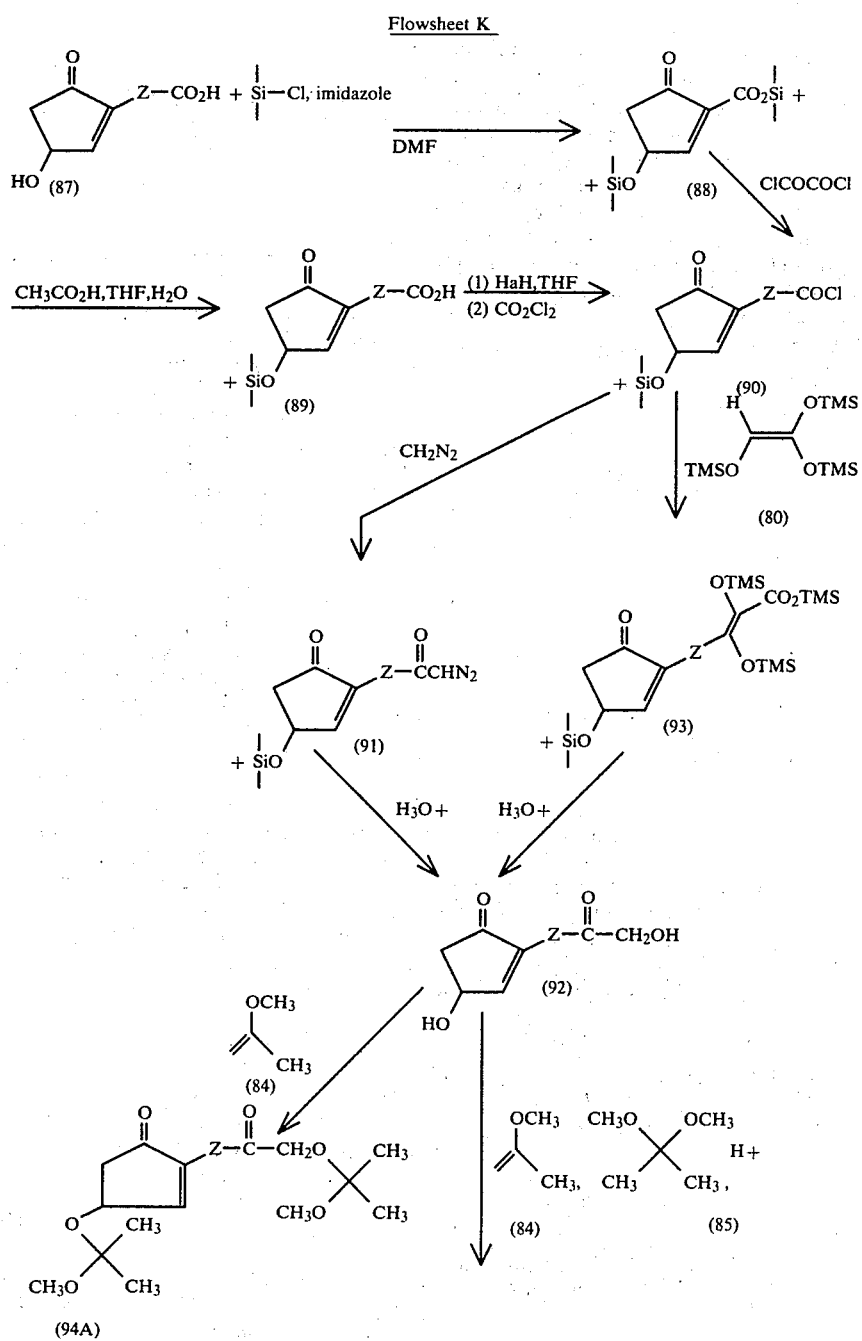

Flowsheet K

Flowsheet K

-continued

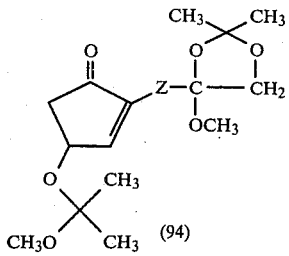

(94)

The preparation of the reagent 1,1,2-tris-trimethylsilyloxyethylene (80) is described hereinbelow in Flowsheet M. The reaction of glycolic acid with 1,1,1,3,3,3-hexamethyldisilazane and trimethylsilylchloride in pyridine gives bis-trimethylsilated glycolic acid (113). Addition of (113) to a tetrahydrofuran solution of one equivalent of lithium 1,1,1,3,3,3-hexamethyldisilazane amide at −78° C. generates a lithium enolate which is trapped with trimethylsilylchloride to produce the desired reagent (80).

FLOWSHEET M

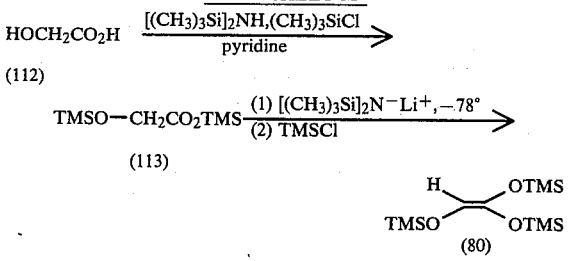

The preparation of the prostaglandin congeners of this invention are described hereinbelow in Flowsheet N wherein Z is $(CH_2)_6$—; $R_3'''$ is 2-methoxy-propyl-2-oxy (—$OC(CH_3)_2OCH_3$) or trimethylsilyloxy; $R_3'''$ is hydroxy; T' is the radical

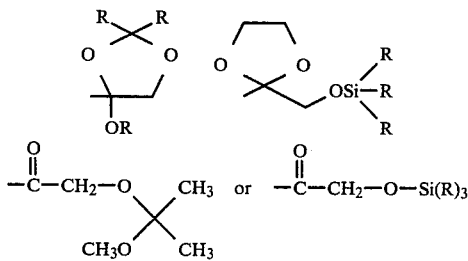

wherein R is as hereinabove defined. R' is selected from the group consisting of:

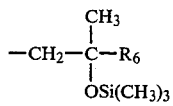

wherein $R_6$ is $C_4$–$C_7$ alkyl.

In accordance with Flowsheet N the vinyliodide (114) is treated with either one equivalent of n-butyllithium or 2 equivalents of t-butyllithium at low temperature, preferably −30° to −70° C. in an inert solvent, e.g., hexane, ether or toluene to provide the trans alkenyl-lithium reagent (116).

Alternatively, the vinyllithium reagent (116) can be prepared by treatment of a vinylstannyl derivative such as (115) with n-butyllithium at −10° to −78° C. in ether or THF.

For the preparation of the asymmetrical lithio cuprate (117) or the like, a solution of one molar equivalent of copper (I)-1-alkyne, preferably copper (I)-1-pentyne, in anhydrous hexamethylphosphorous triamide, preferably one to five molar equivalents, and anhydrous ether is added to one molar equivalent of the aforementioned vinyllithium solution cooled to about −78° C. After about one hour at this temperature, a molar equivalent of the requisite cyclopentenone (120) is added. After several hours at −78° C. to −20° C. the reaction mixture is quenched with aqueous ammonium chloride solution and the blocked product (121) is isolated in the usual manner.

It is also possible to effect conjugate 1,4-addition with the asymmetrical lithio cuprate (119) derived from vinyllithium (116) and cuprous thiophenoxide. A solution of vinyllithium (116) in ether at −78° C. is reacted with an equimolar amount of a reagent prepared by admixture, in ether at a temperature of 0° C. to −78° C., of equimolar amounts of cuprous thiophenoxide and copper (I) iodide tributylphosphonium complex. After about 30 minutes at this temperature, the lithio cuprate (119) is treated with the requisite cyclopentenone (120) as described hereinabove for the conjugate addition with 1-alkynyl lithio cuprate (117).

For the preparation of the symmetrical lithio cuprate (118) one molar equivalent of copper (I) iodide tributylphosphine complex, dissolved in anhydrous ether, is added at about −78° C. to two molar equivalents of the aforementioned vinyllithium (116) solution in hexanes, cooled to −78° C. After about one hour at this temperature, the lithio cuprate (118) is treated with the requisite cyclopentenone (120) as described hereinabove for the conjugate addition with the 1-alkynyl lithio cuprate (117).

The procedures for conjugate addition involving organocopper reagents are well known in the art; see for example, C. J. Sih, et al., J. A. C. S., 97 865 (1975).

All available evidence leads us to believe that the —CH=CH—$R'_2$ function introduced by the cuprate process occupied a position trans to the 11-oxy function. Similarly, we are led to the conclusion that in the product (122) the two side-chains attached to $C_8$ and $C_{12}$ are trans to each other. However, we are not certain of this configurational relationship in the product as it is obtained directly from the cuprate process. These products may have the side chains in a trans- or cis- relationship or they may be a mixture containing both the trans- and cis-isomers. This is indicated in the nomenclature of the compounds involved by the designation 8ε. In order to ensure a trans-relationship in (121) these products can be submitted to conditions known in the literature to equilibrate the cis-8-iso-PGE$_1$ to a mixture containing about 90% of the trans product. These conditions involve treatment with potassium acetate in aqueous methanol for 96 hours at room temperature.

ment of (121) with a mixture of acetic acid, tetrahydrofuran and water (4:2:1) at 25° to 55° C.

When T' is

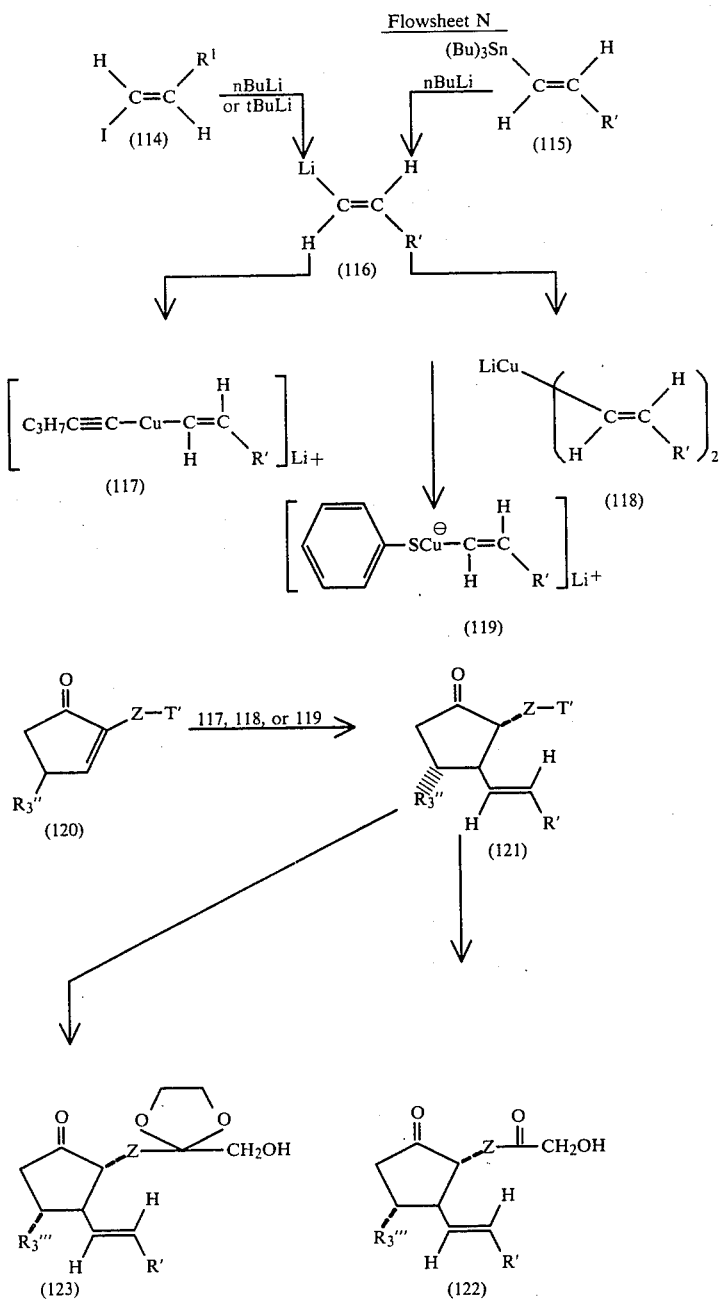

When T' is

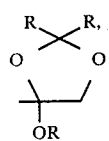

removal of the blocking groups from (121) to give the prostaglandin congener (122) is accomplished by treat-

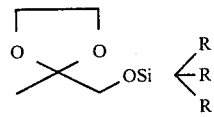

(121) may be deblocked to give ketal (123) by treatment with 0.6 N hydrochloric acid in tetrahydrofuran at room temperature for 4 to 7 hours.

In certain cases it is possible to convert the carboxylic acid function of a prostaglandin congener into a terminal hydroxymethyl ketone function as shown in Flowsheet O hereinbelow wherein Z is $(CH_2)_6$, $C_{13}-C_{14}$ is —CH=CH—trans and R is as hereinabove defined. Treatment of a prostaglandin congener (124), in which the 11-hydroxy group and the hydroxy group of the β-chain are protected with a suitable group such as acetate or a dimethyl-t-butylsilyl ether, with oxalyl chloride in benzene for 2 to 5 hours furnishes the acid chloride (125), wherein $R_3''$ is hydrogen or a protected oxygen group. The protected 11-hydroxyl-acid chloride compound may be prepared in the manner described above in Flowsheet K.

The prostaglandin congeners (124) may be prepared by the 1,4 conjugate addition of the suitably protected cyclopentenones (87) such as (cyclopentenones 88) and the lithiocuprate (117), (118) or (119) by the preparation disclosed herein by the examples and Flowsheet N. Addition of the acid chloride (125), dissolved in ether, to an ether solution of at least three equivalents of diazomethane gives the diazoketone (126). Hydrolysis of the diazoketone using aqueous sulfuric acid and tetrahydrofuran at about 0°–55° C. gives the hydrozymethyl ketone analog (127). The acetate protecting group can be removed by refluxing with acidified methanol. The dimethyl-t-butylsilyl ether protecting group can be removed by treatment with aqueous hydrochloric acid in tetrahydrofuran at 25° to 60° C.

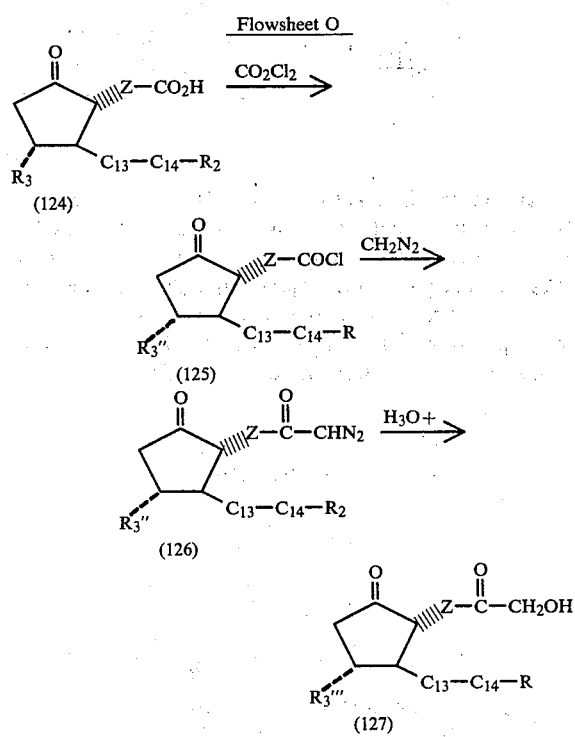

When the compounds of this invention are prepared from racemic starting compounds two racemates are obtained. In appropriate instances these racemates can be separated from each other by careful application of the usual chromatographic procedures. In the more difficult instances it may be necessary to apply high pressure liquid chromatography including recycling techniques. [See. G. Fallick, American Laboratory, 19–27 (August, 1973) as well as references cited therein. Additional information concerning high speed liquid chromatography and the instruments necessary for its application is available from Waters Associates, Inc., Maple Street, Milford, Mass.]

It is also possible to prepare the compounds of this invention in their optically active forms by the conversion of the optically active 4-hydroxycyclopent-2-en-1-one carboxylic acid (128) to the optically active protected hydroxy ketone analog (129) using the methods outlined hereinabove in Flowsheet K.

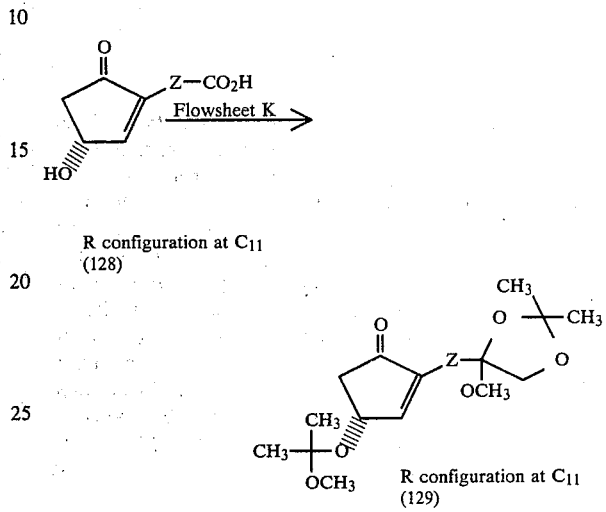

Conjugate addition of the vinyl cuprates to (129) followed by deblocking as described hereinabove in Flowsheet N then gives the compounds of this invention in their optically active forms. Although in some cases two diastereoisomers will be formed, each optically active, they can be separated by chromatographic procedures as described hereinabove.

The preparation of optically active 4-hydroxycyclopent-2-en-1-ones such as (128) is described hereinbelow.

The 4-hydroxycyclopentenone racemates may be resolved into their component enantiomers (130) and (131) by derivatizing the ketone function with a reagent having an optically active center. The resulting diastereomeric mixture can then be separated by fractional crystallization, or by chromatography, or by high speed liquid chromatography involving, if necessary, recycling techniques. Among the useful optically active ketone derivatizing reagents are 1-α-aminoxy-γ-methylpentanoic acid hydrochloride [to give (132), (R)-2-aminoxy-3,3-dimethylbutyric acid hydrochloride, and 4-α-methylbenzyl semicarbazide. After separation of the diastereomeric derivatives, reconstitution of the keto function provides the individual 4-hydroxycyclopentenone enantiomers (130) and (131). A useful procedure for the resolution of a 4-hydroxycyclopentenone racemate via an oxime such as (132) is described in the art [R. Pappo, P. Collins and C.Jung, Tetrahedron Letters, 943 (1973)].

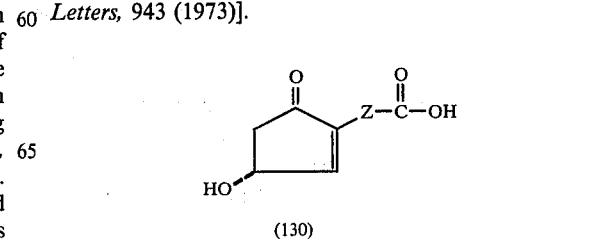

-continued

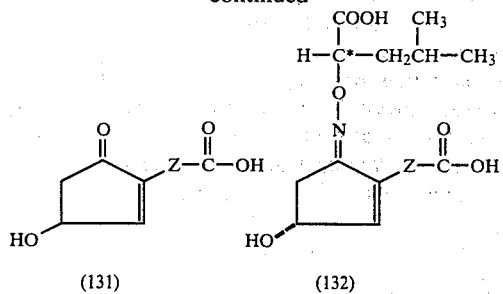

(131) (132)

An alternate procedure for the preparation of the 4(R)-hydroxycyclopentenone enantiomers such as (130) involves as a key step the selective microbiological or chemical reduction of trione (133) to the 4(R)-hydroxycyclopentanedione (134). A wide variety of microorganisms are capable of accomplishing this asymmetric reduction, one of the most useful being *Dipodascus unincleatus*. This step also can be achieved chemically by catalytic hydrogenation in the usual manner (for example, under about one atmosphere of hydrogen in methanol) using a soluble rhodium catalyst with chiral phosphine ligands, such as (1,5-cyclooctadiene)-bis-(o-anisylcyclohexylmethylphosphine)rhodium (I) tetrafluoroborate, in the presence of one equivalent of organic base, such as triethylamine.

Conversion of hydroxycyclopentanedione (134) to an enol ether or enol ester (135, E=alkyl, preferably isopropyl; aroyl such as benzoyl; or arylsulfonyl such as 2-mesitylenesulfonyl) is accomplished by treatment, for example, with isopropyl iodide and a base such as potassium carbonate in refluxing acetone for from 15 to 20 hours, or with a base such as triethylamine and 0.95 equivalents of benzoyl chloride or a slight excess of 2-mesitylenesulfonyl chloride, in a non-prototropic solvent at a temperature of about $-10°$ to $-15°$ C. Reduction of (135) with excess sodium bis(2-methoxyethoxy)aluminum hydride in a solvent such as tetrahydrofuran or toluene at low temperatures, such as $-60°$ to $-78°$ C., followed by mild acid hydrolysis (representative conditions: aqueous dilute hydrochloric acid, pH 2.5; or oxalic acid, sodium oxalate in chloroform) at ambient temperatures from 1 to 3 hours provides the 4(R)-hydroxycyclopentenone ester (136). The ester (136), can then be hydrolized to acid (130).

For a description of these procedures in the art see: C. J. Sih, et al., *J. A. C. S.*, 95, 1676 (1973); J. B. Heather, et al., *Tetrahedron Letters*, 2627 (1972); and R. Pappe, P. Collins, and C. Jung, *Ann. N. Y. Acad. Sci.*, 180, 64 (1971).

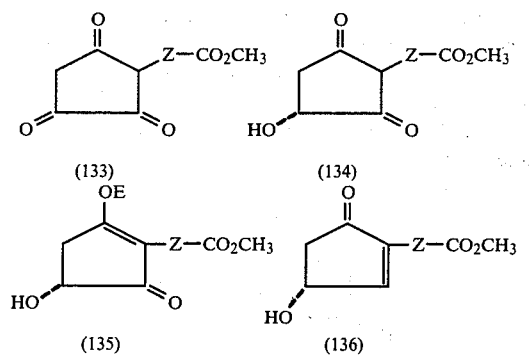

(133) (134)
(135) (136)

Procedures for the preparation of the requisite cyclopentanetriones (133) are well-established in the art and generally involve the treatment of an -1-oxo long chain ester (137) with an alkyl oxulate in the presence of sodium methoxide in methanol, followed by treatment with dilute hydrochloric acid in aqueous methanol to effect the dealkoxalylation of the intermediate (138). See J. Kutsube and M. Matsui, *Agr. Biol. Chem.*, 33, 1078 (1969); P. Collins, C. J. Jung and R. Pappo, *Israel Journal of Chemistry*, 6, 839 (1968); R. Pappo, P. Collins and C. Jung, *Ann. N. Y. Acad. Sci.*, 180, 64 (1971); C. J. Sih. et al., *J. A. C. S.*, 95, 1676 (1973) (see reference 7); and J. B. Heather, et al., *Tetrahedron Letters*, 2313 (1973) for pertinent background literature.

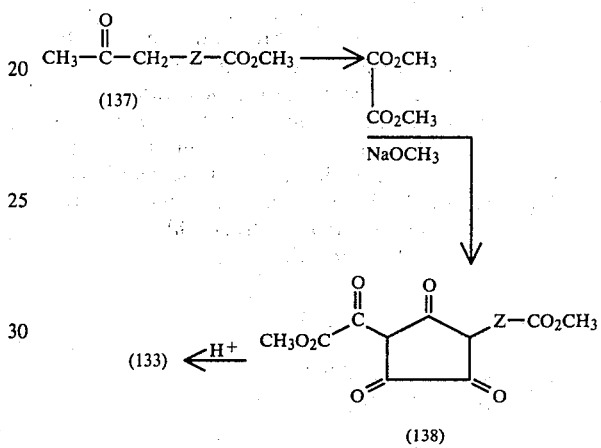

(137)
(133)
(138)

The intermediate keto esters (137) may be prepared by a variety of methods known to the art. One useful procedure is outlined below and involves alkylation of ethyl acetoacetate sodium salt (139) in the usual manner with the appropriate side-chain precursor (140, X=Cl, Br, I, preferably Br or I) followed by decarbethoxylation and reesterification, all in the usual manner.

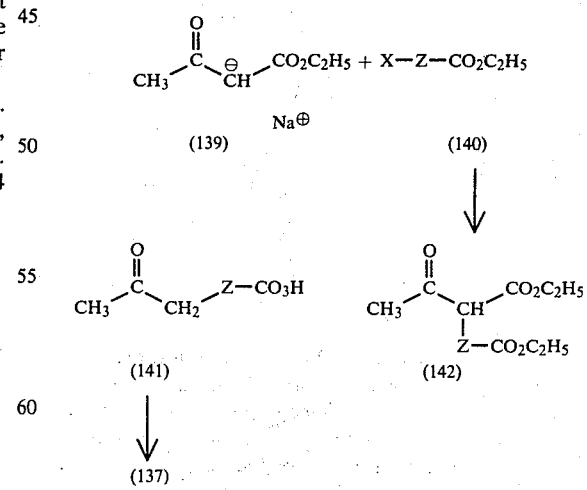

(139) (140)
(141) (142)
(137)

The side-chain precursors (140) are commercially available where Z is $-(CH_2)_p-$, and can be prepared as described in Belgian Pat. No. 786,215 (granted and opened to inspection Jan. 15, 1973).

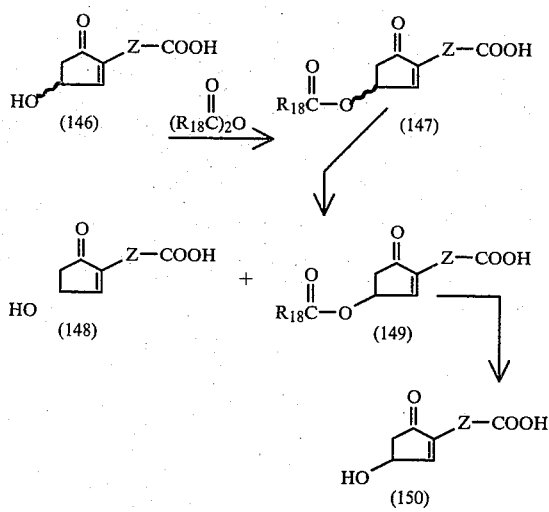

It is also possible to resolve the 4-hydroxycyclopentenone racemate (146) by microbiological means. Thus, treatment of the 4-O-alkanoyl or aroyl derivatives (147, $R_{18}$=aryl or alkyl) of racemate (146) (preferably the 4-O-acetyl and 4-O-propionyl derivatives) with an appropriate microorganism, preferably a Saccharomyces species e.g., 1375-143, affords preferential de-O-acylation of the 4(R)-enantiomer to give (148), which is then separated from the unreacted 4(S)-O-acyl enantiomer (149) by chromatographic procedures. After separation, mild hydrolysis of the 4(S) derivative (149) provides the 4(S)-hydroxycyclopentenone (150). [See N. J. Marsheck and M. Miyano, Biochima et Biphysica Acta, 316, 363 (1973) for related examples.]

It is also possible to prepare the individual 4-hydroxycyclopentenones (148) and (150) directly by selective microbial hydroxylations of the corresponding 4-unsubstituted cyclopentenone (151). For example, with Aspergillus niger ATCC 9142; a selective 4(R)-hdyroxylation of [151, Z=(CH₂)₆] has been reported; see S. Kurozumi, T. Tora and S. Ishimoto, Tetrahedron Letters, 4959 (1973). Other microorganisms can also accomplish this hydroxylation.

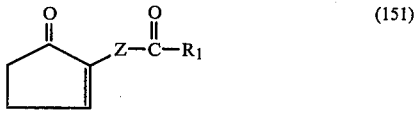

The novel compounds of the present invention have potential utility as hypotensive agents, anti-ulcer agents, agents for the treatment of gastric hypersecretion and gastric erosion, agents to provide protection against the ulcerogenic and other gastric difficulties associated with the use of various non-steroidal anti-inflammatory agents (e.g., indomethacin, aspirin, phenylbutazone), ibuprofen, sulindac, tolmetin, mifananidued, naproxen and the like, bronchodilators, anti-inflammatory agents, abortifacients, agents for the induction of labor, agents for the induction of menses, fertility-controlling agents, oestrus regulators for use in animal husbandry with cattle and other domestic animals and central nervous system regulatory agents. Certain of the novel compounds of this invention possess utility as intermediates for the preparation of the other novel compounds of this invention.

The novel compounds of this invention possess the pharmacological activity described below as associated with the appropriate known prostaglandin types.

The known PGE, PGFα, PGFβ, PGA and PGD compounds are all potent in causing multiple biological responses even at low doses. For example, PGE₁, PGE₂, PGA₁ and PGA₂ are extremely potent in causing vasodepression and smooth muscle stimulation, and also are potent as antilipolytic agents. Moreover, for many applications, these known prostaglandins have an inconveniently short duration of biological activity. In striking contrast, the novel prostaglandin analogs of this invention are substantially more specific with regard to potency in causing prostaglandin-like biological responses, and/or having a substantially longer duration of biological activity.

Therefore, each of these novel prostaglandin analogs of this invention is surprisingly and unexpectedly more useful than one of the corresponding above-mentioned known prostaglandins for at least one of the pharmacological purposes indicated below for the latter, either because it has a different and narrower spectrum of biological activity than the known prostaglandins, and therefore is more specific in its activity and causes smaller and fewer undesired side effects than the known prostaglandins, or because of its prolonged activity, fewer and smaller doses of the novel prostaglandin analog can frequently be used to attain the desired result.

Another advantage of the novel compounds of this invention, compared with the known prostaglandins, is that these novel compounds are administered effectively orally, sublingually, intravaginally, buccally, or rectally, in addition to the usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

PGE₁, PGE₂ PGE₃, dihydro-PGE₁, PGAα, PGFβ and PGA compounds, their esters and pharmacologically acceptable salts, are extremely potent in causing various biological responses. For that reason, these compounds are useful for pharmacological purposes. See, for example, Bergstrome, et al., Pharmacol. Rev. 20, 1 (1968), and references cited herein. A few of those biological responses are systemic arterial blood pressure lowering in the case of the PGA and PGE compounds as measured, for example, in anesthetized (phenobarbital sodium) pentolinium-treated rats with in-dwelling aortic and right heart cannulas; pressor activity, similarly measured for the PGF compounds; stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of PGE compounds, as shown in dogs with secretion stimulated by food or histamine infusion; activity on the central nervous system; decrease of blood platelet adhesiveness in the case of PGE, as shown by platelet-to-glass adhesiveness, and inhibition of blood platelet aggregation and thrombus formation induced by various physical stimuli, e.g., arterial injury, and various biochemical stimuli, e.g.—ADP, ATP, serotonin, thrombin, and collagen, and in the case of the PGE and PGA compounds, stimulation of epidermal proliferation and keratinization, as shown when they are applied in culture to embryonic chick and rat skin segments.

Because of these biological responses, these known prostalandins are useful to study, prevent, control, or alleviate a wide variety of disease and undesirable physiological conditions in birds and mammals including humans, useful domestic animals, pets, and zoological speciments, and in laboratory animals, e.g., mice, rats, rabbits, and monkeys.

For example, these compounds are useful in mammals, including man, as nasal decongestants. For this purpose, the compounds are used in a dose range of about 10 mg to about 10 mg per ml of a pharmacologically suitable liquid vehicle or as an aerosol spray, both for topical application.

PGA, PGFβ and PGE compounds are useful as hypotensive agents to reduce blood pressure in mammals including man. For this purpose, the PGFβ compounds are administered by intravenous infusion at the rate of about 0.01 mg to about 40 mg per Kg of body weight per minute, or in a single dosage or multiple doses of about 25 mg to 2500 mg per Kg of body weight total per day. The PGE and PGA compounds are administered by intravenous infusion at the rate of about 0.01 to about 50 mg Kg of body weight per minute, or in a single dose of multiple doses of about 25 to 2500 mg per Kg of body weight total per day.

The PGE, PGFα and PGFβ compounds are useful in place of oxytocin to induce labor pregnant female animals, including humans, cows, sheep and pigs, at or near term or in pregnant animals with intrauterine death of the fetus from about 20 weeks to term. For this purpose, the PGF compound is infused intraveneously at a dose of 0.01 mg to 50 mg per Kg of body weight per minute until or near the termination of the second stage of labor, i.e., expulsion of the fetus. Similarly, the PGE compound is infused intravenously at a dose of 0.01 to 50 mg per Kg of body weight per minute until or near the expulsion of the fetus. These compounds are especially useful when the female is one or more weeks postmature and natural labor has not started, or 12 to 60 hours after the membranes have ruptured and natural labor has not yet started.

The PGE, PGFα and PGFβ compounds are useful for controlling the reproductive cycle in ovulating female mammals, including humans and other animals. For that purpose, $PGF_{2\alpha}$, for example, is administered systemically at a dose level in the range of 0.01 mg to about 20 mg per Kg of body weight, advantageously during a span of time starting approximately at the time of ovulation and ending approximately at the time of menses or just prior to menses. Likewise, a PGE compound is administered in the same fashion at a dose level of 0.01 mg to about 50 mg per Kg of body weight. Additionally, expulsion of an embryo or fetus is accomplished by similar administration of the compound during the first third or the second third of the normal mammalian gestation period. Accordingly, such compounds are useful as abortifacients. They are also useful for induction of menses during approximately the first two weeks of a missed menstual period and thus, are useful as contraceptive anti-fertility agents.

11α-hydroxy-PGE compounds are extremly potent in causing stimulation of smooth muscle, and are also highly active in potentiating other known smooth muscle stimulators, for example, oxytocic agents, e.g., oxytocin, and the various ergot alkaloids including derivaties and analogs thereof. Therefore $PGE_2$, for example, is useful in place of or in combination with less than usual amounts of these known smooth muscle stimulators for example, to relieve the symptoms of paralytic ileus, to control or prevent uterine bleeding after abortion or delivery, to aid in expulsion of the placenta, and during the puerperium. For the latter purpose, the PGE compound is administered by intravenous infusion immediately after abortion or delivery at a dose in the range about 0.01 to about 50 mg per Kg of body weight per minute until the desired effect is obtained. Subsequent doses are given by intravenous, subcutaneous, or intramuscular injection or infusion during puerperium in the range of 0.01 to 2 mg per Kg of body weight per day, the exact dose depending on the age, weight, and condition of the patient or animal.

The novel PGE compounds of this invention are also useful as bronchodilators for the treatment of asthma and chronic bronchitis. As such they may be conveniently administered by inhalation of aerosol sprays prepared in a dose range of about 10 ug to about 10 mg/ml of a pharmacologically suitable liquid vehicle. Relative to the natural prostaglandins, these PGE compounds have the significant advantage of inducing prolonged effects.

The PGE compounds are also useful in mammals, including man and certain useful animals, e.g., dogs and pigs, to reduce and control excessive gastric secretion, thereby reducing or avoiding gastric erosion or gastrointestinal ulcer formation, and accelerating the healing of such ulcers already present in the gastrointestinal tract. For this purpose, the compounds are injected or infused intravenously, subcutaneously, or intramuscularly in an infusion dose range of about 0.001 mg to about 0.01 mg per Kg of body weight per minute, or in a total daily dose by injection or infusion in the range of about 0.1 to about 1 mg per Kg of body weight per day, the exact dose depending on the age, weight, and condition of the patient or animal, and on the frequency and route of administration. Most conveniently they are administered orally 1-4 times/day for a total daily dose of about 0.003 mg to about 0.1 mg/Kg of body weight. These compounds may also be useful in conjunction with various non-steroidal anti-inflammatory agents, such as aspirin, phenylbutazone, indomethacin and the like, to minimize the well-known ulcerogenic effects of the latter.

The PGE compounds of this invention are also useful as topical vasodilators.

The $PGE_1$ compounds of this invention are useful whenever it is desired to inhibit platelet aggregation, to reduce the adhesive character of platelets, and to remove or prevent the formation of thrombi in mammals including man, rabbits, and rats. For example, these compounds are useful to treat and prevent myocardial infarcts and post-operative thrombosis. For these purposes, these compounds are administered systemically, e.g., orally, intravenously, subcutaneously, intramuscularly, and in the form of sterile implants for prolonged action. For rapid response, especially in emergency situations, the intravenous route of administration is preferred. Doses in the range of about 0.005 to about 20 mg per Kg of body weight per day are used, the exact dose depending on the age, weight, and condition of the patient or animal, and on the frequency and route of administration.

It is well known that platelet aggregation inhibitors may be useful as anti-thrombotic drugs. Inhibition of platelet aggregation can be conveniently measured in vitro by monitoring changes in optical density and/or light transmission in platelet rich plasma upon addition of suitable aggregating agents such as adenosine diphosphate, epinephrine, thrombin or collagen. Alternatively, platelet aggregation can be measured in vitro using platelet rich plasma obtained at various time intervals from animals given inhibitors by an oral or parenteral route.

The PGE compounds of the present invention exhibit the ability to inhibit platelet aggregation in vitro when tested by the following procedure.

Human protein rich plasma is incubated with modified Tyrode's solution in a proportion of 40–50% human protein rich plasma. The test compounds are added at varying concentrations and after 5 minutes incubation, an aggregating agent such as adenosine diphsophate or collagen is added. The change in optical density (light transmission) is monitored by eye and inhibition is recorded as a (−) or lack of inhibition is recorded as a (+). Test compounds are considered active if they inhibit adenosine diphosphate or collagen induced aggregation at a concentration of 0.025 mg/ml or less within 5–10 minutes.

The PGE compounds of this invention also have bronchodilator activity as determined in a test using dogs anesthetized, artificially ventilated and submitted to a continuous respiratory spasm induced by pilocarpine.

Mongrel dogs of either sex weighing between 5 and 10 kg are used. They are premedicated with morphine HCl by subcutaneous injection at 1.5 mg/Kg. An intravenous perfusion of 5% (W/V) chloralose is started ½ hour after the morphine injection in such a way that 60 mg/Kg are administered within 15 minutes. After completion, a continuous perfusion of 10 mg/Kg/hour is maintained throughout the experiment. The dogs are artificially ventilated by means of a Starling pump at a rate of 20 breaths/minute. The volume is adjusted according to the weight of the animal. [Kleinman and Radford, *J. Appl. Physiol.,* 19, 360 (1964)]. All the measurements are made with the dogs positioned supine in a heated, V-shaped table. Curarization is obtained by succinylcholine chloride using a starting injection of 3 mg/Kg lasting 3 minutes, followed by a continuous perfusion of 0.1 mg/Kg/minute.

The respiratory spasm is induced by a starting injection of 400 mcg/Kg of pilocarpine HCl lasting 5 minutes. An increase or decrease in the dose of pilocarpine HCl may occur as a function of the observed effect on the airway's resistance. A 15 minute delay is observed before the start of a continuous perfusion of pilocarpine HCl at a dose of 4 mcg/Kg/minute to maintain a constant spasm during the test.

A metallic cannula is inserted and fixed, after tracheometry, into the upper part of the trachea. The two cephalic veins and two femoral veins are catheterized to inject the various agents. The femoral artery is catheterized to measure the systemic blood pressure. An esophageal balloon (11 cm×2.5 cm) is inserted into the lower third of the oesophagus to measure the endothoracic pressure. The measurement of air flow is made with a Fleish pneumotachograph connected to the tracheal tube.

The transpulmonary pressure is measured as follows: The tracheal cannula is equipped with a stainless steel axial tube (1.5 -m) which is closed at its distal end and projected 2.5 cm beyond the end of the cannula. Three holes with a diameter of one mm are pierced on this latter segment. This tube, which is used to measure the tracheal pressure, is connected to one of the two chambers of a Sanborn 267 B/C differential transducer. The other chamber is connected to the esophageal balloon by means of a polyethylene catheter of the same length and characteristics as the balloon's.

The airflow is measured from the Fleish pneumotachograph by means of a Sanborn 270 differential transducer.

The tidal volume is obtained by electronic integration of the flow signal using an R.C. integrator.

The systemic and pulmonary blood pressures are gauged by means of a Sanborn 267 B/C or 1280B pressure transducer.

An electrocardiogram is taken in lead 2. Its use is to monitor a cardiac rate-meter.

All these parameters are recorded on a Sanborn polygraph. The transpulmonary pressure and the tidal volume are also displayed as rectangular coordinates on an oscilloscope.

The airway's resistance, expressed in cm of water/liter/second, is measured by substracting from the electrical equivalent of the transpulmonary pressure, a voltage proportional to the flow so as to synchronize the pressure and volume signals on the oscilloscope [Mead and Whittenberger, *J. Appl. Physiol.,* 5, 779 (1953)].

The value of the pulmonary elastance, expressed in cm of water/liter, is obtained by means of the same principal, i.e., an electrical signal proportioned to the volume is subtracted from the transpulmonary pressure signal, in order to optimize the pressure-flow loop on the oscilloscope.

The details of this method are described by Lulling, et al. [*Med. Pharmacol. Exp.,* 16, 481 (1967)].

The computing operations are carried out with an analogical computer which allows the direct reading, cycle to cycle, of the values of resistance and elastance.

The test compounds are administered by an Aerosol ® route. The micronebulizer of a Bird Mark 7 respirator is fitted on the metallic cannula just after the pneumotachograph. The "puff" of the test compound, in Aerosol ® is driven by a 2 Kg/cm² pressure, allowed into the micronebulizer just during one inspiration cycle. The micronebulizer is fitted on the respiratory tube only during the "puff." It is weight just before and just after administration to determine the amount of test compound administered.

The % inhibition of spasms induced by pilocarpine for a representative compound of this invention is shown below in Table A. Approximately 50 mg of the solution is administered to each dog.

TABLE A

Bronchodilator Activity (Pilocarpine Assay) % Inhibition of Spasm

| | | % Inhibition of pilocarpine induced spasm as a function of time after drug administration | | |
|---|---|---|---|---|
| | Dose mg/ml | 2 min. | 35 min. | 60 min. |
| 1,9-dioxo-11α,16-dihydroxy-16-methyl-1-hydroxymethyl-13-trans- | | | | |

TABLE A-continued

Bronchodilator Activity (Pilocarpine Assay) % Inhibition of Spasm

| | Dose mg/ml | % Inhibition of pilocarpine induced spasm as a function of time after drug administration | | |
|---|---|---|---|---|
| | | 2 min. | 35 min. | 60 min. |
| prostene | 3.2 | 90 | 70 | 45 |

The bronchodilator activity of some of the PGE compounds of this invention is determined in guinea pigs against bronchospasms elicited by intravenous injections of 5-hydroxy-tryptamine, histamine or acetylcholine by the Konzett procedure. [See J. Lulling, P. Lievens, F. El Sayed and J. Prignot, *Arzneimittel-Forschung*, 18, 995 (1968)].

In the Table B which follows, bronchodilator activity for a representative compound of this invention against three spasmogenic agents is expressed as an $ED_{50}$ determined from the results obtained with three logarithmic cumulative intravenous doses.

TABLE B

Bronchodilator Activity (Konzett Assay) ED 50 mg/Kg

| | Spasmogenic Agent | | |
|---|---|---|---|
| | 5-Hydroxy-tryptamine | Histamine | Acetylcholine |
| 1,9-dioxo-11α,16-dihydroxy-16-methyl-1-hydroxymethyl-13-trans-prostene | $3.0 \times 10^{-3}$ | $943 \times 10^{-6}$ | $4.7 \times 10^{-3}$ |

PROTOCOL FOR EVALUATION OF GASTRIC ANTI-SECRETORY AGENTS

A. MODEL:

Unanesthetized mongrel dogs weighing 10-15 Kg are used. The animals have a surgically prepared denervated (Heidenhain) pouch which drains by gravity through a titanium cannula. These animals are trained to stand quietly in a Pavlov support. Gastric secretion is stimulated at the lowest rate giving stable secretion (25-40% of maximal) with histamine acid phosphate, 30-50 μg/Kg/hr. Under such stimulation, a stable gastric secretory output can generally be maintained for a period of at least 3 hours.

Gastric juice is collected continuously during secretory studies and pooled into 15-minute collections. Determination of collection volume, pH and titratable acidity is performed. Acid is determined by titrating an aliquot of gastric sample with 0.1 N NaOH to pH 7.0 using an automatic titrator.

Drugs are administered on a background of submaximal gastric secretory stimulation and the results compared with control secretory studies without the use of drug. Depending upon the duration of action of a particular drug, it may be possible for a single drug-secretory study to serve as its own control. The route of drug administration is oral administration into the main stomach. This route is easy to perform and does not interfere with the smooth collection of pouch gastric juice.

Gastric Acid Secretion in the Dog Fistula

Three mongrels dogs (20-32 kg) were surgically prepared with stainless steel cannulae. These were inserted into the most dependent portion of the ventral stomach and exteriorized through the abdomen for the collection of gastric secretions. The dogs were trained to stand quietly in a Pavlov support and were conscious during subsequent secretory studies.

TABLE E

Effect of 1,9-dioxo-11α,16-dihydroxy-16-methyl-1-hydroxymethyl-13-trans-prostene (compound A) on the Gastric Acid Secretion[a] in the Dog Fistula Preparation

| treatment | dose (μg/kg) I.G.) | n[b] | cumulative two-hour gastric secretion[c] | |
|---|---|---|---|---|
| | | | volume (ml) | acid (mEq H+) |
| control | — | 20 | 130 ± 11 | 17.2 ± 1.6 |
| Compound A | 10 | 6 | 59 ± 19 (p 0.01) | 6.9 ± 2.8 (p 0.005) |

[a]After a 26-hour fast, gastric acid secretion was submaximally stimulated, beginning 45 minutes after treatment, using a constant intravenous infusion of histamine acid phosphate (40 μg/kg/hr). [b]Each of three dogs was treated six to seven times with vehicle (control) and one to three times with each compound; n is the number of experiments conducted with each treatment. [c]Total secretion from 45-120 minutes following intragastric (I.G.) administration of drugs or vehicle. Mean effects of treatment were compared to control means by Student's t test. Compound A is 1,9-dioxo-11α,16-dihydroxy-16-methyl-1-hydroxymethyl-13-transprostene.

Restraint—Immersion Stress Ulcers in the Rat (Wilson)

A. Induction of Ulcers

Male "Sprague-Dawley Derived" rats (Licke-Erickson Laboratories, Maywood, Ill.) weighing 150 to 200 g, are fasted, and provided drinking water for 16 to 19 hours prior to the start of the study. At 0 time the rats are dosed orally with compound or vehicle, (approximately 0.5 ml) and then secured in a Bollman-type restraining cage. Five minutes after dosing, the animals are immersed (tail downward) to "shoulder level" into a 22° C. water bath for 100 minutes. At the end of this period, the animals are decapitated and their stomachs promptly excised with about 5 mm each of esophagus and duodenum.

With a blunt tipped scissor the stomach is opened along the greater curvature, starting at the tip of the rumen through the glandular mucosa into the pylorus and opening the bit of diodenum along its amesenteric border. Debris is removed from stomach by rinsing in saline at room temperature and gently blotting it with gauze or filter paper. The stomach is then spread out, mucosal surface upward on a 3×5 file card or similar material.

B. Evaluation of Lesions

With an illuminated magnifier the lesions are counted (for total lesion count) and scored (for weighted score) after the method described by G. Osterloh, et al., Arzneimittel-Forschung, 16 (8a):901910, August 1966. The score for each lesion is given in the following table, modified from the paper.

| LESION TYPE | SCORE |
|---|---|
| No lesions | 0 |
| Erythema | 1 |
| Petechial Hemorrhages | 2 |
| Erosion | 3 |
| Pinpoint Ulcer | 4 |
| Small Ulcer (0.5-1 mm) | 5 |

-continued

| LESION TYPE | SCORE |
|---|---|
| Medium Ulcer (1–3 mm) | 6 |
| Large Ulcer (3 mm) | 7 |
| Perforation | 8 |

Very large (area) non-perforating leasions are frequently seen. These are measured as so many 3 mm diameter ulcers and scored as multiples of #7. For example, a 3 mm$^2$ diameter ulcer is taken to have an area of 7.1 mm$^2$, so a lesion measuring 9×4 mm will have an area of 36 mm$^2$ and hence is equivalent to 5 lesions with a score #7.

TABLE F
Effect of Prostaglandin on Stress-Induced (Immersion) Ulcers in Rats

| Compound | Dose (mg/Kg P.O.) | Ulcer Score [Mean ± SEM (n)] | % Reduction |
|---|---|---|---|
| Control |  | 40 ± 5 (27) |  |
| A* | 500 | 7 ± 2 (6) | 82 (p .01) |
|  | 200 | 13 ± 7 (13) | 67 (p .005) |
|  | 80 | 7 ± 6 (7) | 82 (p .005) |
|  | 16 | 6 ± 4 (6) | 85 (p .005) |
|  | 5 | 15 ± 11 (6) | 62 (p .05) |

Rats were dosed by gavage with compound or vehicle and submerged into a 22° C. water bath for 100 minutes. At the end of this period, animals were sacrificed and their stomachs removed and scored for ulcers.
A* is: 1,9-dioxo-11α,16-dihydroxy-16-methyl-1-hydroxymethyl-13-trans-prostene.

Indomethacin-Induced Ulcers in the Rat

Male Wistar rats (Royal Hart, New Hampton, N.Y.), weighing 190–210 g are distributed among control and treatment groups (5 rats/group) and housed one rat per cage. During the 52 hour test period, the rats are permitted free access to food and drinking water for the first 33 hours but are fasted overnight prior to sacrifice. Indomethacin is suspended (4 mg/ml) in a 1.5 starch-phosphate buffer solution (SPBS). CL 115,574 is dissolved in 10 mg/ml in ethanol and then diluted in SPBS to 0.1 mg/ml or to a lower concentration as required. The indomethacin suspension is injected subcutaneously (10 mg/kg) and the prostaglandin suspension is given by gavage (0.5 mg/kg or less) b.i.d. on day 0 and 1. Rats receive only one dose of prostaglandin and indomethacin on day 2 and 6 hours later are killed with chloroform. The stomachs are dissected, opened along the greater curvature, and rinsed briefly in tap water. They are then spread, mucosal surface facing upward and pinned onto uniform size corks (2.5 inch diameter) individually numbered on the back. The identification number for each stomach is unknown to the inventigator and the stomachs re randomly graded according to the following scheme (10).

0—Normal
1—Petechial Hemorrhage, or pin-point ulcers
2—One or two small ulcers or hemorrhagic erosions
3—Many areas of hemmorrhage erosion or ulcers, a few large
4—Massive areas of hemorrhagic erosion or many ulcers, mainly large Intestines are also removed and examined for the presence of ulcers, which are graded according to the scheme outlined below.

0—Normal
1—Mucosa thin, petechial hemmorrhage
2—"Blow-outs", when intestine inflated with air
3—Few ulcers. Gut more fragile than normal, tears along line of mesentery attachments when removed
4—Many large perforating lesions. Adhesions. Gut hemmorrhagic and very fragile. Tears readily and cannot be removed intact. Graded in situ.

TABLE G
Effect of 1,9-dioxo-11α,16-dihydroxy-16-methyl-1-hydroxymethyl-13-trans-prostene (Compound A) on Indomethacin-Induced Ulcers in Rats

| Treatment[a] | | | Gastric Ulcer | Intestinal Ulcer | |
|---|---|---|---|---|---|
| Indomethacin (mg/kg subcut.) | Compound A (mg/kg P.O.) | N | Score (Mean ± S.E.M.) | Score (Mean ± S.E.M.) | Hematocrit (Mean ± S.E.M.) |
| 10 | — | 10 | 2.9 ± 0.2 | 3.7 ± 0.2 | 33.1 ± 2.1 |
| 10 | .5 | 10 | 2.1 ± 0.4 | 2.0 ± 0.4[b] | 40.0 ± 1.4[b] |
| 10 | .1 | 10 | 1.7 ± 0.3[b] | 2.7 ± 0.2[b] | 41.1 ± 2.4[b] |
| 10 | .02 | 8 | 1.9 ± 0.4[b] | 3.5 ± 0.2 | 35.6 ± 1.9 |
| — | — | 10 | 0.3 ± 0.2[b] | 0[b] | 48.0 ± 0.6[b] |

[a]Treatment is B.I.D. on days 0 and 1, and once a day 2, six hours prior to sacrifice for scoring.
[b]Significantly different from indomethacin-only treatment at p <.05.

The novel compounds of this invention induce the biological responses described hereinabove as associated with their particular prostaglandin types. These novel compounds are accordingly used for the above-described corresponding purposes. These derivatives described hereinabove are also more selective in their biological action and generally induce a more prolonged effect than the corresponding natural prostaglandins. These preparations are novel, completely unanticipated and provide distinct and important advantages.

In addition, certain of the novel compounds of this invention are useful for the preparation of other novel compounds of their invention.

The invention will be described in greater detail in conjunction with the following specific examples.

The following examples describe the manner and process of making and using the invention, but are not to be construed as a limitation thereon.

EXAMPLE 1

Preparation of 1,9-dioxo-11α,16-dihydroxy-16-methyl-1-hydroxymethyl-13-trans-protene A. To a stirred solution of 75.5 g (150 mmol total vinylstannane; estimated 120 mmol of trans-isomer by CMR) of E-1-tri-n-butylstannyl-4-methyl-4-trimethylsilyloxy-1-octene in 120 ml of THF at −78° initially was added 60 ml of 2.0 M n-butyllithium in hexane during 5 min. so that the temperature was < −60°. The light amber solution was warmed to −40° during 10 min. and maintained at the temperature for 2 hr. The solution was recooled to −78° for use in paragraph C.

B. To a well-stirred 17.25 g (132 mmol) sample of copper pentyne was added 48 ml (about 43.1 g, or 264 mmol) of freshly distilled hexamethyl-phosphorous triamide. After 20 min. 300 ml of ether was added. The resulting clear, light yellow solution was cooled to −78° for 60 minutes.

C. To the vinyllithium solution prepared in paragraph A at 78°, initially was added the precooled solution of copper complex prepared in paragraph B via double trip needle technique during 10 min. so that the temperature was <−65°. The resulting light amber solution was stirred at −78° for 60 minutes.

D. To the stirred solution prepared in paragraph C at −78° initially was added a solution of 23.07 of (60.0 mmol) of 1-(1-methoxy-1-methylethoxy)-8-[3-(1-methoxy-1-methylethoxy)-5-oxo-1-cyclopenten-1-yl]-2-octanone in 50 ml of ether during 10 min. so that the temperature was <−65°. The syringe and septum bottle were washed with 10 ml ether. After 5 min. the light amber solution was warmed to −40° during 10 min. The solution was stirred at −40° for 1.5 hr. and then allowed to warm to −20° during 30 min. and then recooled to −78°. The reaction was quenched by addition of a solution of 14.4 ml (about 240 mmol) of gl HOAc in 100 ml ether. The precipitate which formed was stirrable with a nagnetic stirrer on this scale.

E. The mixture above was transferred with the aid of washing with 750 ml of ether into a stirred, ice-cold mixture of 480 ml of N/L HCl and 240 ml of satd NH4CL. The mixture was stirred vigorously at 0°–5° for 5 minutes. The aqueous phase was separated and extracted with 350 ml of ether. The combined organic phases were washed successively with 2×240 ml of ice-cold N/L HCl, 240 ml of half-satd brine, 240 ml of 1:1 satd brine-satd NaHCO3, 240 ml of half-satd brine, and 3×240 ml satd brine. The solution was dried over MgSO4, filtered through a small pad of Celite, and concentrated in vacuo at ca 30° to give 108 g of mobile light yellow liquid.

F. The materials from paragraph E resulting from this run (60 mmol-scale, 108 g) and a similar run (57.7 mmol-scale, 103 g) were combined. This material (211 g) was treated with a solution prepared from 940 ml of gl HOAc, 470 ml of THF, and 235 ml of water. The resulting solution was stirred at 40°–43° for 60 min. Some (n-Bu)4Sn was not dissolved. The mixture was diluted with 600 ml of toluene. Then 600 ml of distillate was removed via rotary evaporator at about 30°. The flask which ocntained the solution was set up for standard vacuum distillate (dry-ice acetone cooled receiver). The solution was diluted with 600 ml of toluene. Then 600 ml of distillate was removed (both at about 30°, 0.1 mm). The solution was diluted with 600 ml of toluene. Then the volume of the solution was reduced to about 1000 ml. The solution was diluted with 600 ml of toluene. Then the volume was reduced to about 500 ml. The solution was diluted with 300 ml of toluene (total toluene used was 2700 ml). This solution was evaporated to give 194 g of a mixture of colorless (n-Bu)4Sn and a dark amber oil.

G. The material from paragraph F was placed, with the aid of repeated hexane wash, on the top of a pad of 385 g of Mallinckrodt SilicaAr CC-7 silica gel contained in a glass column; dimensions 5.8×30 cm. The column was washed with 2500 ml of hexane to remove stannane material. The column was then washed with 4000 ml of ethyl acetate, taking care to wash all hexane-insoluble material in flask and on column sides onto the top of the silica gel. The first 3250 cc of ethyl acetate eluate yielded 77.4 g of amber oil on evaporation. The last 750 ml of eluate yielded 0.1 g of amber oil (total=77.5 g).

H. Chromatography. To a 5.4 cm diameter column filled with 2:1 heptane ethyl acetate was added 970 g of Mallinckrodt SilicAr CC-7 silica gel. The column stood overnight; dimensions 5.4×98 cm. This column was used to purify most of the material from paragraph G (71.0 g).

The material (71.0 g) was dissolved in 250 ml of 2:1 heptane-ethyl acetate and 50 ml of ethyl acetate (required to produce solution). The solution was developed on the above-described column. Elution was carried out under slight nitrogen pressure to produce a flow rate of about 3–4 l/hr.

Fractions which emerged from the column were examined by TLC with the solvent system 20:1 EtOAc-MeOH. Plates were developed by spraying first with 2,4-DNP solution and then cupric acetate solution and charring.

The column was eluted with heptane-ethyl acetate block gredients according to the following schedule:

| Batch | Volume (l) | Solvent Ratio |
|---|---|---|
| 1 | 7 | 2:1 heptane-EtOAc |
| 2 | 7 | 5:3 heptane-EtOAc |
| 3 | 12 | 3:2 heptane-EtOAc |
| 4 | 2 | 4:3 heptane-EtOAc |
| 5 | 2 | 10:9 heptane-EtOAc |
| 6 | 4 | 1:1 heptane-EtOAc |
| 7 | 2 | 3:2 EtOAc-heptane |
| 8 | 2 | 2:1 EtOAc-heptane |
| 9 | 6 | 3:1 EtOAc-heptane |
| 10 | 12 | 3:1 EtOAc-heptane Increased to pure EtOAc |

Fractions collected were of ap-ropriate size (about 1500–2000 ml) and were pooled according to TLC as above. The product emerged from the column corresponding to solvent batches 6–10 above to provide 16.9 g of product. By the method described hereinabove and starting with E-1 tri-n-butylstannyl-4-methyl-4-trimethylsilyloxy-1-octene and 1-(1-methoxy-1-methylethoxy-8-[3(R)-1(1-methoxy-1-methylethoxy)-5-oxo-1-cyclopenten-1-yl]-6-octenone, nat-1,9-dioxo-11α,16(R)-dihydroxy-16-methyl-1-hydroxymethyl-13-trans-prostene and nat-1,9-dioxo-11α,16(S)-dihydroxy-16-methyl-1-hydroxy-methyl 13-trans-prostene are prepared.

I claim:

1. An optically active compound of the formula:

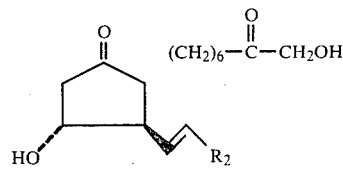

wherein R2 is

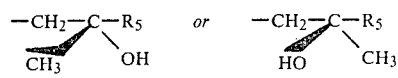

wherein $R_5$ is selected from the group consisting of $C_4$–$C_7$ alkyl and the racemic mixture thereof.

2. The optically active compound according to claim 1, nat(16R/S)-1,9-dioxo-11α-dihydroxy-16-methyl-1-hydroxymethyl-13-trans-prostene, and the corresponding racemic mixture thereof.

3. The optically active compound according to claim 1, nat(16S)-1,9-dioxo-11α,16-dihydroxy-16-methylhydroxymethyl-13-trans-prostene, and the corresponding racemic mixture thereof.

4. The optically active compound according to claim 1, nat(16R)-1,9-dioxo-11α,16-dihydroxy-16-methyl-1-hydroxymethyl-13-trans-prostene, and the corresponding racemic mixture thereof.

* * * * *

UNITED STATES PATENT AND TRADEMARK OFFICE
CERTIFICATE OF CORRECTION

PATENT NO. : 4,299,988
DATED : November 10, 1981
INVENTOR(S) : Allan Wissner

It is certified that error appears in the above—identified patent and that said Letters Patent is hereby corrected as shown below:

The term of this patent subsequent to March 3, 1998, has been disclaimed.

Signed and Sealed this

Nineteenth Day of January 1982

[SEAL]

*Attest:*

*Attesting Officer*

GERALD J. MOSSINGHOFF

*Commissioner of Patents and Trademarks*

UNITED STATES PATENT OFFICE
CERTIFICATE OF CORRECTION

Patent No. 4,299,988                    Dated November 10, 1981

Inventor(s) ALLAN WISSNER

It is certified that error appears in the above-identified patent and that said Letters Patent are hereby corrected as shown below:

In Claim 1, column 28, the structure should read as follows:

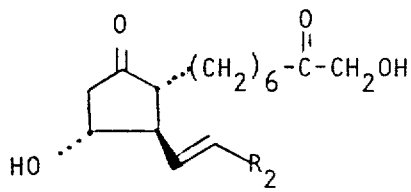

and not as in the patent.

Signed and Sealed this

Sixth Day of April 1982

[SEAL]

Attest:

Attesting Officer

GERALD J. MOSSINGHOFF

Commissioner of Patents and Trademarks